(12) United States Patent
Irion et al.

(10) Patent No.: US 7,588,569 B2
(45) Date of Patent: Sep. 15, 2009

(54) MEDICAL INSTRUMENT FOR THE TREATMENT OF TISSUE BY MEANS OF A HIGH-FREQUENCY CURRENT AND MEDICAL SYSTEM WITH A MEDICAL INSTRUMENT OF THIS TYPE

(75) Inventors: Klaus M. Irion, Liptingen (DE); Ulrich Hagelauer, Konstanz (DE)

(73) Assignee: Karl Storz GmbH & Co. KG (DE)

( * ) Notice: Subject to any disclaimer, the term of this patent is extended or adjusted under 35 U.S.C. 154(b) by 570 days.

(21) Appl. No.: 10/946,936

(22) Filed: Sep. 22, 2004

(65) Prior Publication Data

US 2005/0065513 A1 Mar. 24, 2005

Related U.S. Application Data

(63) Continuation of application No. PCT/EP03/02956, filed on Mar. 21, 2003.

(30) Foreign Application Priority Data

Mar. 22, 2002 (DE) ................................ 102 12 841

(51) Int. Cl.
*A61B 18/18* (2006.01)
*A61B 5/05* (2006.01)
(52) U.S. Cl. ............................ 606/46; 600/424; 606/41
(58) Field of Classification Search ............. 606/32–52; 600/117, 424
See application file for complete search history.

(56) References Cited

U.S. PATENT DOCUMENTS

| 5,273,025 | A | 12/1993 | Sakiyama et al. ............... 128/6 |
|---|---|---|---|
| 5,318,025 | A | 6/1994 | Dumoulin et al. ........ 128/653.2 |
| 5,353,795 | A | 10/1994 | Souza et al. ............. 128/653.2 |
| 5,391,199 | A * | 2/1995 | Ben-Haim .................. 607/122 |
| 5,507,743 | A | 4/1996 | Edwards et al. ............... 606/41 |
| 5,558,091 | A | 9/1996 | Acker et al. ............. 128/653.1 |
| 5,828,770 | A | 10/1998 | Leis et al. .................... 382/103 |
| 5,954,648 | A | 9/1999 | Van Der Brug ............. 600/411 |
| 6,135,946 | A | 10/2000 | Konen et al. ................. 600/117 |
| 6,190,382 | B1 | 2/2001 | Ormsby et al. ................. 606/33 |
| 6,236,205 | B1 | 5/2001 | Ludeke et al. ............... 324/318 |
| 6,246,896 | B1 * | 6/2001 | Dumoulin et al. ........... 600/411 |
| 6,288,785 | B1 | 9/2001 | Frantz et al. ................. 356/614 |
| 6,322,559 | B1 | 11/2001 | Daulton et al. ................ 606/41 |
| 6,346,105 | B1 | 2/2002 | Tu et al. |

(Continued)

FOREIGN PATENT DOCUMENTS

DE 297 07 276 U1 7/1997

(Continued)

*Primary Examiner*—Michael Peffley
(74) *Attorney, Agent, or Firm*—St. Onge Steward Johnston & Reens LLC (57) ABSTRACT

The invention relates to a medical instrument for treating tissue by means of high-frequency current. The inventive instrument comprises at least one electrode that can be impinged upon with a high-frequency current and that is disposed on the distal end of an elongated electrode carrier. At least one electromagnetically active position sensor is disposed in the distal zone of the electrode carrier in the direct vicinity of the at least one electrode in such a manner that it detects the intracorporeal position and/or location of the at least one electrode. The invention further relates to a medical system that comprises such an instrument.

17 Claims, 3 Drawing Sheets

U.S. PATENT DOCUMENTS

| | | | |
|---|---|---|---|
| 6,385,482 B1 | 5/2002 | Boksberger et al. | 600/424 |
| 6,477,396 B1 * | 11/2002 | Mest et al. | 600/374 |
| 6,484,049 B1 * | 11/2002 | Seeley et al. | 600/426 |
| 6,961,602 B2 * | 11/2005 | Fuimaono et al. | 600/374 |

FOREIGN PATENT DOCUMENTS

| | | |
|---|---|---|
| DE | 197 55 782 A1 | 6/1999 |
| DE | 695 14 238 T2 | 5/2000 |
| DE | 102 12 841 A1 | 9/2003 |
| EP | 0 890 117 B1 | 3/1997 |
| EP | 1 096 268 A2 | 2/2001 |
| WO | WO 97/36192 | 2/1997 |
| WO | WO 97/40763 | 11/1997 |
| WO | WO 97/45064 | 12/1997 |
| WO | WO 99/30182 | 6/1999 |
| WO | WO 00/53079 | 9/2000 |
| WO | WO 00/53115 | 9/2000 |
| WO | WO 02/08793 A1 | 1/2002 |

\* cited by examiner

MEDICAL INSTRUMENT FOR THE TREATMENT OF TISSUE BY MEANS OF A HIGH-FREQUENCY CURRENT AND MEDICAL SYSTEM WITH A MEDICAL INSTRUMENT OF THIS TYPE

CROSS REFERENCE TO RELATED APPLICATIONS

The present application is a continuation of pending International patent application PCT/EP 2003/002956 filed on Mar. 21, 2003 which designates the United States, and which claims priority of German patent application 102 12 841.3 filed on Mar. 22, 2002.

BACKGROUND OF THE INVENTION

The invention relates to a medical instrument for the treatment of tissue by means of high-frequency current, comprising at least one electrode which can be supplied with high-frequency current and is arranged at a distal end of an elongate electrode carrier.

The invention also relates to a medical system comprising a medical instrument of this type.

An instrument of the type mentioned at the outset is known from WO 00/53079.

An instrument of the type mentioned at the outset is used in high-frequency surgery. High-frequency surgery is used therapeutically in various specialized medical disciplines such as, for example, urology, gynaecology, neurosurgery, abdominal surgery, etc. Specifically in urology and gynaecology, prostatic tissue or endometrial tissue is removed endoscopically by means of an instrument mentioned at the outset, which is also referred to as a resectoscope. The endoscopic HF-aided prostatic resection of benignly enlarged prostates is one of the most common endoscopic therapies. By means of the electrode which can be subjected to high-frequency current, which may be of a monopolar or bipolar design, in the latter case with two electrodes formed as opposite poles being provided, tissue is removed and/or coagulated and/or vaporized under the thermal effect of the high-frequency current. The at least one electrode is, for example, designed in the form of a loop and is therefore often also referred to as a loop or HF loop.

Currently, HF-surgical interventions by means of an instrument of the type mentioned at the outset, for example in the case of prostatic resection or resection of tumours in the thin-walled urinary bladder, are visually monitored endoscopically. For this purpose, the instrument is conventionally coupled to an endoscope optical system. Visual monitoring of the therapeutic intervention is inadequate however. In particular, the setting of the cutting depth of the electrode cannot be visually observed or projected as an image by endoscopic means. If cutting goes too deep, lesions occur to uninvolved tissue, for example of the prostate capsule in the case of prostate resection. Monitoring the depth of penetration of the electrode in the tissue could in principle be made possible by the use of image generating and, specifically, sectional-image generating methods such as ultrasound, X-ray, computer tomography or magnetic resonance. Navigating and locating systems of this type are already known for surgery or endoscopy. A basic prerequisite for navigation by means of such ultrasound, computer-tomography, magnetic-resonance or other image information is, however, the positional or orientational determination of the instrument with respect to a spatial reference, for example in such a way that the position of the instrument can be coupled positionally correctly into the image.

However, positional and/or orientational determination by means of ultrasound or infrared is unsuitable for sensing a position of an instrument in the body, since for such systems there is no visual contact with the location to be determined of the instrument in the body. Another possibility is a direct mechanical coupling of the instrument via position encoders to outside the body, which however is very disadvantageous on account of the great overall space required from outside the body to inside the body.

The document U.S. Pat. No. 5,273,025 discloses a device with which the position and orientation of a portion of a flexible shaft of an endoscope inserted into the body can be determined electromagnetically. For this purpose, arranged in the flexible shaft of the endoscope are one or more coils, which are excited by an electromagnetic field which is generated outside the body and coupled into the body through the surface of the body. The voltage which is induced in the coils by the external electromagnetic field and the intensity of which depends on the orientation of the coils in relation to the electromagnetic field is carried via a line through the shaft of the endoscope to an evaluating device outside the body and evaluated for the positional and orientational determination.

A further system for the electromagnetic determination of the spatial position and/or orientation of one or more objects is disclosed by EP 1 096 268 A2. This known system uses a coil which is excited by an electromagnetic field generated outside the body and which is fastened on the object of which the position and/or orientation is to be determined. The object of which the position or orientation is to be determined is in that case a flexible element, which can, for example, be inserted into a catheter.

SUMMARY OF THE INVENTION

The present invention is based on the object of improving a medical instrument for the treatment of tissue by means of high-frequency current to the extent that the depth of penetration of the electrode into the tissue to be treated can be monitored as exactly as possible in order to avoid lesions to uninvolved tissue being caused by the electrode.

According to an aspect of the invention, a medical instrument for the treatment of tissue by means of high-frequency current is provided, comprising an elongate electrode carrier having a longitudinal axis, a distal region, a distal end and a proximal end; at least one electrode arranged at said distal end of said electrode carrier which electrode can be supplied with high-frequency current; and at least one electro-magnetically acting position sensor arranged in said distal region of said electrode carrier immediately adjacent to said at least one electrode, said position sensor being arranged to produce an electrical signal when exposed to a magnetic field and thereby to sense at least one of a position and an orientation of said at least one electrode.

According to another aspect of the invention a medical system is provided, comprising a medical instrument according to the invention.

The design according to the invention of the electrode carrier with at least one electromagnetically acting position sensor, which is arranged immediately adjacent to the at least one electrode, allows the depth of penetration of the at least one electrode in the tissue to be treated to be determined exactly by means of the position and/or orientation sensing and to be graphically represented in relation to a spatial reference, if appropriate in conjunction with an image system such as, for example, an ultrasound system or a magnetic resonance system. The arrangement of the at least one position sensor in the immediate proximity of the electrode has the advantage that the relative orientation between the electrode and the position sensor during the manipulation of the instrument by the doctor is invariable, as a result of which a particularly exact positional and/or orientational determination of the electrode, and consequently of the depth of penetration into the tissue to be treated, can be monitored. This is required in particular because the electrode carrier of an instrument of this type is customarily formed by an elongate linkage which elastically bends when the electrode is pressed onto tissue.

In a preferred refinement, the at least one position sensor is embedded in the body of the electrode carrier near the electrode.

In this case it is of advantage that the position sensor does not protrude from the electrode carrier and represent a mechanical obstacle or itself become damaged when the instrument is being used for treating tissue. Cleaning of the instrument is also made easier in this way, or not made any more difficult in comparison with an instrument without positional determination.

In a particularly preferred refinement, the position sensor is a coil.

The use of a coil, in particular a miniaturized coil, which according to the previously mentioned refinement may be embedded in the body of the electrode carrier near the electrode, has the advantage that the instrument with the modified electrode carrier can be produced without any significant extra cost in comparison with a conventional electrode carrier. The use of a coil has the advantage that, with a coil, already five degrees of freedom of the position and orientation of the coil and consequently of the electrode can be sensed, that is the position of the coil in a system of Cartesian spatial coordinates and also, in addition, the rotational orientation of the coil about two axes which are perpendicular to each other and perpendicular to the coil axis.

In this case it is further preferred if the coil is arranged with its coil axis substantially parallel to the longitudinal direction of the electrode carrier.

This measure has the advantage, on the one hand, that the coil can be embedded in this orientation into the elongate body of the electrode carrier near the electrode and, on the other hand, that in this way the spatial orientation of the coil in relation to the electrode is well-defined in a simple relation. The single degree of freedom which cannot be sensed by this position of the coil is a rotation of the instrument or electrode carrier about the coil axis. A further advantage of this incorporation of the position sensor is that the outer contour of the sensor-carrying electrode carrier does not change with respect to the standard electrode carrier, at least in the distal region, as a result of which the electrode carrier and electrode are compatible with existing resectoscopes having an endoscope.

In a further preferred refinement, the at least one position sensor is arranged outside the longitudinal center axis of the electrode carrier.

In this case it is of advantage, for example if, as described above, the position sensor is a coil which is arranged in the longitudinal direction of the electrode carrier, that a rotation of the electrode carrier, and consequently of the electrode, about the longitudinal center axis of the electrode carrier can be sensed by the one coil.

If, as is customary in the case of conventional instruments of this type, the electrode carrier has two carrier parts arranged next to each other, it is further preferred if the at least one position sensor is arranged on or in the one carrier part, while the HF supply line for the electrode is arranged in the other carrier part.

In this case it is of advantage that the position sensor is spaced adequately far away from the HF supply line, so that a disturbance of the positional determination on account of the high-frequency current can be minimized as much as possible or excluded. As a result, the positional determination can take place very accurately. It may preferably be additionally envisaged to provide the HF supply line in the other carrier part additionally with a shield, in order to exclude completely disturbing influences caused by electromagnetic fields going back to the high-frequency current supply.

In this connection it is preferred if an electrical line connected to the position sensor runs through the carrier part on which the position sensor is arranged up to a proximal end of this carrier part.

In connection with the previously mentioned preferred design, consequently, in the case of a two-part electrode carrier the one carrier part is used for the HF supply lead, while the other carrier part is used entirely for the positional and/or orientational determination, without other geometrical and structural changes having to be made to the electrode carrier in comparison with a conventional electrode carrier and a conventional electrode. An electrode carrier according to the present invention can therefore also be combined with conventional instrument shafts and endoscopes. Depending on the type of electromagnetic position-sensing system used, the position sensor is driven and/or the signals generated by the position sensor are led to outside the body, for example to an evaluating device, via the electrical line connected to the position sensor.

In a further preferred refinement, the proximal end of the carrier part on or in which the at least one position sensor is arranged is formed as a plug-in contact, so that it can be connected to a socket on an instrument housing part by axial insertion.

In this case it is of advantage that the handling of the instrument does not differ with regard to the assembly or incorporation of the electrode carrier with the electrode in an instrument housing or instrument shaft from such a conventional instrument which does not have position sensing for the at least one electrode.

In a further preferred refinement, at least a second electromagnetically acting position sensor is provided on the electrode carrier.

In this case it is of advantage that, for example in connection with the design of the at least one position sensor as a coil, its coil axis is arranged substantially parallel to the longitudinal direction of the electrode carrier; the still invariant degree of freedom of a rotational orientation of the electrode about the coil axis can be sensed by means of the second position sensor, whereby complete positional sensing of the at least one electrode is made possible with only two position sensors. This additional position sensor can likewise be arranged in the distal region of the electrode carrier or on the opposite carrier part or preferably in a proximal region of the electrode carrier, or even on an extracorporeal part of the instrument. This additional position sensor may in the latter case also be, for example, an optical sensor.

In this case it is further preferred if the second position sensor is a coil arranged substantially with its coil axis transversely in relation to the longitudinal axis of the electrode carrier.

The medical system according to the invention comprises an instrument according to one or more of the preceding designs.

In a preferred refinement of the system it comprises an extracorporeal magnetic-field generator, which generates by means of tetrahedrally arranged coils an inhomogeneous magnetic field, by means of which the at least one position sensor can be excited.

A magnetic-field generator of this type is sold by the company Mednetix AG, Switzerland, under the trade name AURORA and, on account of its compact design, is suitable in particular for use in surgery.

In a further preferred design of the system it comprises an evaluating device which evaluates the position signals generated by the at least one position sensor with regard to the position and/or orientation of the electrode in correlation with a spatial reference.

The evaluating device makes it possible to process the signals generated by the position sensor into positional information, which then can be used preferably for the navigation of the instrument in surgical use.

In this case it is further preferred if an image generating system is present, and if the positional information evaluated by the evaluating device is transmitted to the image generating system for the purpose of graphic representation of the position and/or orientation of the electrode in relation to the spatial reference.

This design allows the doctor operating the instrument to monitor the position and/or orientation of the electrode in or on the tissue, for example by carrying out a cut or a coagulation or a vaporization, if for example the operating site itself is represented as the spatial reference.

If the system is further equipped in the customary way with an HF generator for generating the high-frequency current to which the at least one electrode is subjected, it is envisaged in a further preferred refinement that a driving device is provided for the high-frequency current supply and the magnetic-field generator and/or the evaluating device and/or the position sensor, which device deactivates the high-frequency current supply when the magnetic-field generator or the evaluating device or the position sensor is activated, and vice versa.

This measure has the advantage that it is possible to exclude the possibility of the high-frequency current with which the tissue is to be treated disturbing or falsifying the positional or orientational determination of the at least one electrode. In other words, a positional determination is carried out only when no therapeutic high-frequency current is flowing, and vice versa.

In a further preferred refinement an interlocking circuit which alternately makes possible the high-frequency current supply to the electrode and the position sensing by means of the position sensor via two direct electrical electrode supply lines is provided.

In this case it is of advantage that the high-frequency current application and the positional or orientational determination of the at least one electrode can be operated via only two, jointly used, direct electrical supply lines, one of which preferably in each case may be arranged in one of the two carrier parts of the electrode carrier arranged next to each other. This achieves the effect of a simple construction of the electrode carrier along with the electrode that is almost symmetrical apart from the presence of the position sensor in one of the two carrier parts, and, furthermore, only two plug-in contacts are necessary for the functions stated above.

Further advantages and features will be apparent from the following description and the accompanying drawing.

It goes without saying that the features stated above and those still to be explained below can be used not only in the combination respectively specified but also in other combinations or on their own without departing from the scope of the present invention.

BRIEF DESCRIPTION OF THE DRAWINGS

An exemplary embodiment is represented in the drawing and described in more detail hereafter with reference to the said drawing, in which.

DETAILED DESCRIPTION OF A PREFERRED EMBODIMENT

Figure 1:
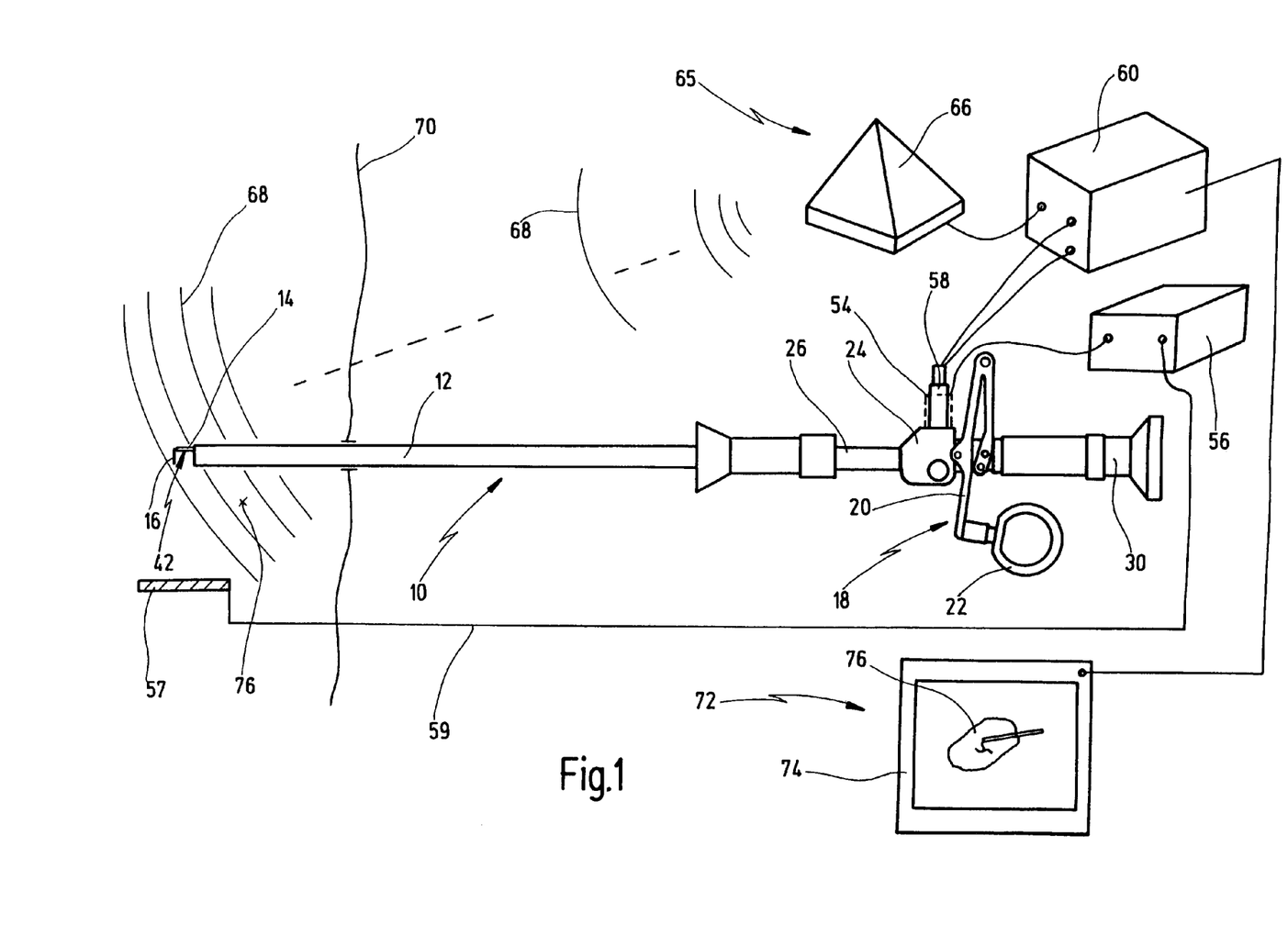
FIG. 1 shows a medical instrument for the treatment of tissue by means of high-frequency current in side view together with a schematic representation of a medical system of which the instrument in FIG. 1 forms a component part.

Represented in FIG. 1 is a medical instrument provided with the general reference numeral 10 for the treatment of tissue by means of high-frequency current. The instrument 10 is also referred to as a resectoscope.

Figures 2, 3:
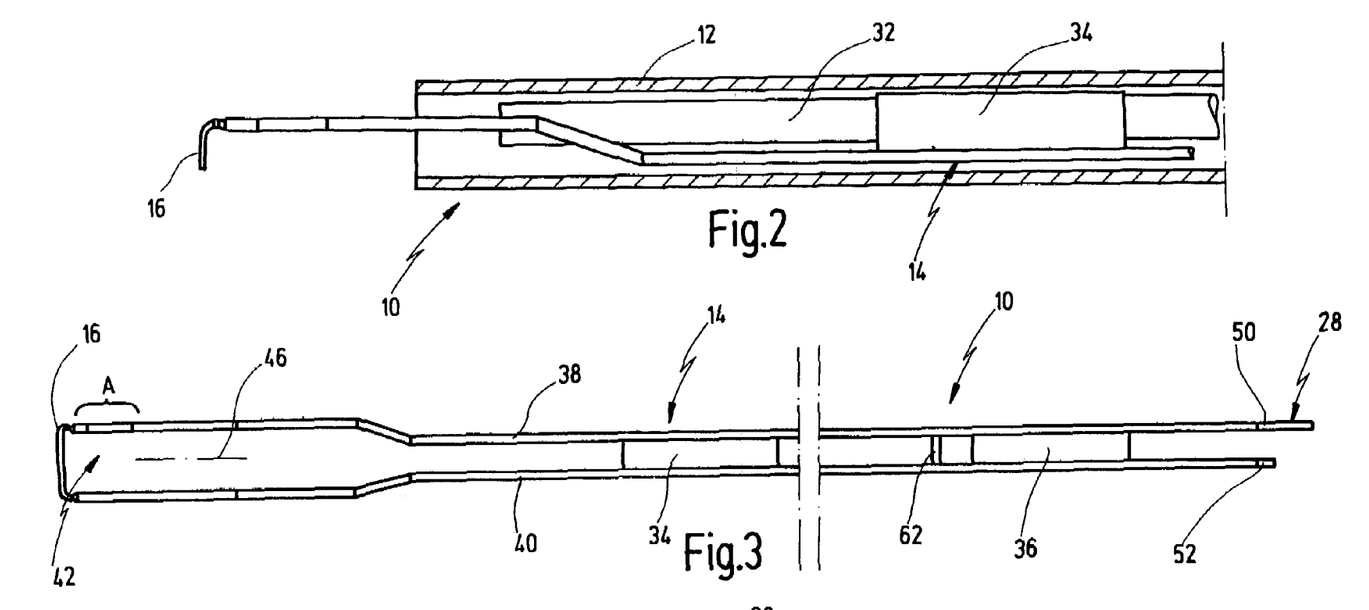
FIG. 2 shows a longitudinal section through a distal portion of the instrument in FIG. 1 on an enlarged scale, an electrode and electrode carrier of the instrument being represented in side view in FIG. 2.
FIG. 3 shows a plan view of the entire electrode carrier and the electrode in FIG. 2 on their own.
Figure 4:
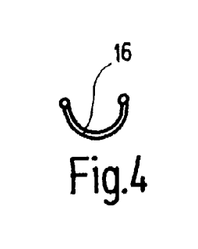
FIG. 4 shows a view from the front of the electrode in FIGS. 2 and 3.

The instrument 10 has an elongate shaft 12, in which there is arranged, according to FIG. 2, an electrode carrier 14, at the distal end of which an electrode 16 which can be supplied with high-frequency current is arranged. As FIG. 4 reveals, the electrode 16 is formed as a loop. With the electrode 16, tissue can be cut, coagulated and/or vaporized under the effect of high-frequency current.

The electrode carrier 14 and the electrode 16 are displaceable in relation to the shaft 12, the electrode carrier 14 and the electrode 16 being represented in FIG. 2 in a position in which they have been pushed out of the shaft 12. The electrode 16 can be completely retracted into the shaft 12.

To be able to displace the electrode carrier 14 and the electrode 16 axially in relation to the shaft, a handle 18 is provided at the proximal end of the instrument 10. The handle 18 has a movable arm 20, on which an operating element 22 is fastened, and which is articulated on a housing part 24. The housing part 24 is for its part connected to a sleeve 26, which together with the housing part 24 is axially movable in relation to the shaft 12.

The electrode carrier 14 is connected by its proximal end 28 (FIG. 3) to the housing part 24, as further explained hereafter.

Through the shaft 12 of the instrument 10 there also extends an endoscope optical system, which according to FIG. 1 has an eyepiece 30 and an endoscope shaft 32 as shown in FIG. 2 and connected to the latter. The endoscope shaft 32 is immovable in relation to the shaft 12, while the electrode carrier 14 is guided in a sliding manner on the endoscope shaft 32 by means of clamps 34 and 36 (FIGS. 2 and 3).

The electrode carrier 14 has a first carrier part 38 and a second carrier part 40, the two of which are arranged alongside each other and run substantially parallel to each other.

The two carrier parts 38 and 40 are fixed on each other by means of the clamps 34 and 36. Nevertheless, the electrode carrier 14 is relatively unstable and can bend when pressure is applied to the tissue to be treated via the electrode 16.

To this extent, the electrode carrier 14 along with the electrode 16 does not differ substantially from a conventional electrode carrier and a conventional electrode.

Figure 5:
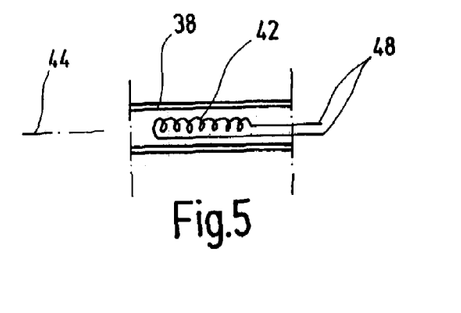
FIG. 5 shows a schematic representation of the detail A in FIG. 3 on a still further enlarged scale.

A major difference between a conventional electrode carrier and the electrode carrier 14 is that, in a distal region of the electrode carrier 14 of the electrode 16 denoted in FIG. 3 by A, there is arranged immediately adjacent to the electrode 16 an electromagnetically acting position sensor 42 which, according to FIG. 5, is formed as a coil. The position sensor 42 makes it possible to sense the intracorporeal position and orientation of the electrode 16 when the instrument 10 is being used, for example in a prostatic resection, and consequently also the depth of penetration of the electrode 16 into the tissue to be treated, as described hereafter.

The position sensor 42 in the form of the coil is in this case embedded in the body of the electrode carrier 14, to be more specific in the body of the first carrier part 38 near the electrode 16, as schematically illustrated in FIG. 5. In the region of the coil, the carrier part 38 is made of a material which acts in a non-shielding or non-distorting manner with respect to electromagnetic fields.

The position sensor 42 in the form of the coil is in this case arranged with the coil axis 44 parallel to the longitudinal direction of the electrode carrier 14.

The coil forming the position sensor 42 has a diameter of less than 2 mm, preferably less than 1 mm, and has a length in the range of approximately 5-10 mm.

With the coil forming the position sensor 42 it is possible to determine the spatial position and orientation of the electrode 16 with respect to a spatial reference in the three Cartesian spatial directions x, y and z, and also the rotational orientation of the electrode 16 about two axes perpendicular to the coil axis 44, and perpendicular to each other.

As revealed by FIG. 3, the position sensor 42 is, furthermore, arranged outside the longitudinal center axis 46 of the electrode carrier 14, so that a rotation of the electrode 16 about the longitudinal center axis 46 of the electrode carrier 14 can be sensed by the position sensor 42. The position sensor 42 is unable to sense a rotation of the electrode 16 about the coil axis 44 of the coil forming the position sensor 42.

While the position sensor 42 is arranged in the first carrier part. 38 of the electrode carrier 14, the HF supply line (not represented) for the electrode 16 runs exclusively in the second carrier part 40, to be precise from the electrode 16 up to the proximal end 28 of the electrode carrier 14.

In the first carrier part 38 there runs on the other hand an electrical line 48 connecting the position sensor 42, to be precise from the position sensor 42 up to the proximal end 28 of the electrode carrier 14. The electrical line 48 serves as a signal line for the signals generated by the position sensor 42 as a result of electromagnetic excitation through the first carrier part 38 to the proximal end and outside the body. Instead of signal transmission by means of an electrical line, however, telemetric or wireless signal transmission to outside the body may also be provided.

As in the case of a conventional electrode carrier, the first carrier part 38 has at the proximal end 28 of the electrode carrier 14 a plug-in contact 50 and the second carrier part 40 has a plug-in contact 52, via which the electrode carrier 14 is snap-locked in the housing 24 of the instrument 10. As a difference from a conventional electrode carrier, however, only the plug-in contact 52 of the electrode carrier 14 serves for being connected to an HF generator 56 via an HF plug connection 54 (FIG. 1), in order to supply the electrode 16 correspondingly with high-frequency current. A neutral electrode 57, which customarily lies outside the body, on the body of the patient, is likewise connected to the HF generator 56 via an electrical line 59.

The plug-in contact 50 of the first carrier part 38 is likewise inserted in the conventional way into a corresponding socket in the housing part 24 (not represented), but is in connection via the latter with a further plug connection 58 which is arranged alongside the HF plug connection 54 and via which the instrument 10 is connected to an activating/evaluating device 60, which serves for the positional and orientational determination of the electrode 16.

According to FIG. 3, arranged on the electrode carrier 14, at a further proximal point of the electrode carrier 14, is a second electromagnetically acting position sensor 62, which may likewise be formed as a coil and is arranged with its coil axis substantially transversely in relation to the longitudinal direction of the electrode carrier 14. By means of this second position sensor 62, the invariance of the positional determination with respect to a rotation of the electrode 16 about the coil axis 44 of the coil forming the first position sensor 42 can then be overcome, so that the spatial position and orientation of the electrode 16 can then be definitively determined, whereby the penetration of the electrode 16 into the tissue to be treated can be monitored very well.

Schematically represented in FIG. 1 along with the medical instrument 10 is a medical system 65, to which the instrument 10 belongs.

Along with the instrument 10, the system 65 comprises the already mentioned HF generator 56 and also the driving/evaluating device 60.

In addition, the system 65 has a magnetic-field generator 66, which generates an electromagnetic field 68 outside the body, the electromagnetic field 68 being coupled into the body through the surface 70 of the body.

The magnetic-field generator 66 has tetrahedrally arranged, pulsed-excited coils, by means of which the electromagnetic field 68 is generated as an inhomogeneous field, the position sensor 42 being excited by the field 68. Depending on the orientation and position of the position sensor 42 in relation to the inhomogeneous electromagnetic field 68, a corresponding signal is generated in the position sensor 42 and is then transmitted to outside the body. The magnetic-field generator 66 thereby generates a series or set of, for example six, different spatial magnetic field geometries or distributions, each of which is sensed by the position sensor 42. Each series of different magnetic field distributions generates a series of signals in the position sensor 42. The processing of the series of signals in the driving/evaluating device 60 then makes it possible to determine the position and orientation of the position sensor 42, and consequently the position and orientation of the electrode, 16 in relation to a spatial reference which is in a fixed relationship with the magnetic-field generator 66.

The magnetic-field generator 66 is, for example, a magnetic-field generator sold under the trade name AURORA by the company Mednetix AG, Switzerland.

The signals generated by the position sensor 42 on account of the interaction with the electromagnetic field 68 radiated in outside the body are transmitted via the plug connection 58 to the driving/evaluating device 60 and evaluated there for determining the position and orientation of the electrode 16 in correlation with a spatial reference, for example the operating site or the body of the patient.

The system 65 further comprises an image generating system 72, of which only the visual-display device in the form of a screen is represented in FIG. 1. The image generating system 72 may be, for example, an ultrasound, computer tomography, optical coherence tomography or magnetic resonance system, with which it is possible to obtain sectional images of the operating site and present them on the visual-display device 74. In FIG. 1, the operating site presented in this way is provided with the reference numeral 76. The positional information evaluated by the driving/evaluating device with respect to the position and/or orientation of the electrode 16 is transmitted for the graphic representation of the position and/or orientation of the electrode 16 in relation to the operating site 76 to the image generating system 72 and graphically presented on the visual-display device 74 in spatial correlation with the operating site 76. In this way, the positional and/or orientational determination of the electrode 16 can be used for the navigation of the instrument 10 in the operating site 76.

Like the instrument 10, the magnetic-field generator 66 is connected to the driving/evaluating device 60. The HF generator 56 is also connected to the activating/evaluating device 60. The driving/evaluating device 60 deactivates the HF generator 56 when the magnetic-field generator 66 is activated, and vice versa. In this way, no positional and/or orientational determination of the electrode 16 takes place when the electrode 16 is supplied with high-frequency current, and vice versa. A falsification or disturbance of the positional determination of the electrode 16 is reliably avoided as a result.

According to a second aspect of the invention, a medical system comprising an instrument of the afore-mentioned kind is provided.

Figure 6:
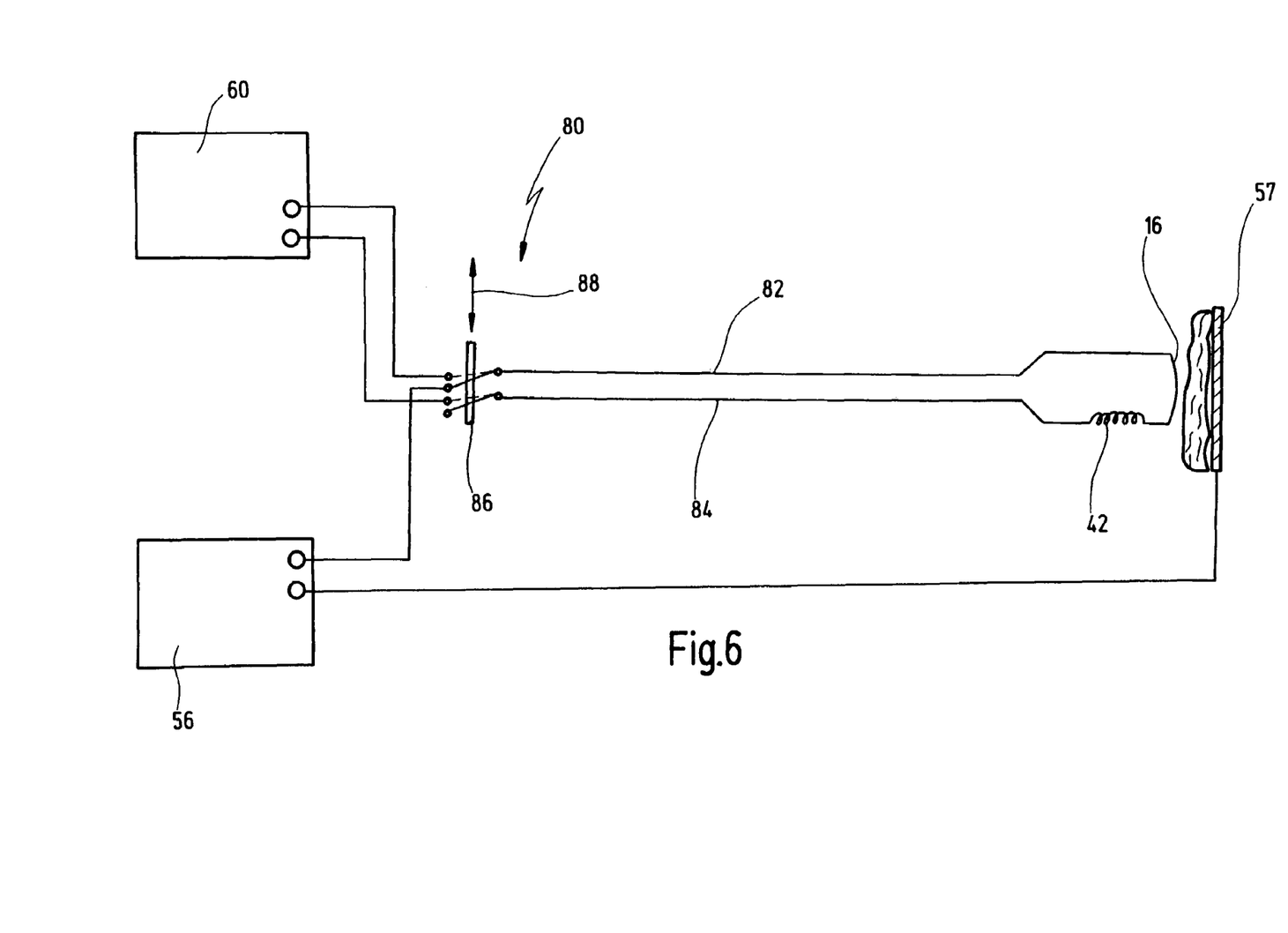
FIG. 6 shows a block diagram of the interlocking circuit for the alternate high-frequency current supply to the electrode and positional determination of the electrode.

For this purpose, the driving device 60 according to FIG. 6 has, for example, an interlocking circuit 80, which alternately makes possible the high-frequency current supply to the electrode 16 and the position sensing by means of the position sensor 42 via two direct electrical electrode supply leads 82 and 84. The electrode supply leads 82 and 84 are alternately connected by means of a changeover switch 86 to the driving/evaluating device 60 and the HF generator 56. In the operational position of the changeover switch 86 represented by solid lines in FIG. 6, the supply leads 82 and 84 are connected to the HF generator 56, so that in this position of the changeover switch 86 the electrode 16 is subjected to high-frequency current. In the operational position of the changeover switch 86 represented by interrupted lines, the supply leads 82 and 84 are connected to the driving/evaluating unit 60, whereby the electrode supply leads 82 and 84 connect the position sensor 42 in the form of the coil for the positional determination of the electrode 16 to the driving/evaluating device 60. The alternate switching over of the changeover switch 86 according to the double-headed arrow 88 may in this case automatically take place periodically or aperiodically according to a predetermined clock or else by means of a manual actuating device (not represented), which can be actuated by the doctor operating the instrument.

What is claimed is:

1. A medical instrument for the treatment of tissue by means of high-frequency current, comprising:
    an elongate electrode carrier having a longitudinal axis, a distal region, a distal end and a proximal end;
    at least one electrode arranged at said distal end of said electrode carrier which electrode can be supplied with high-frequency current;
    at least one electro-magnetically acting position sensor arranged in said distal region of said electrode carrier immediately adjacent to said at least one electrode, said position sensor being arranged to produce an electrical signal when exposed to a magnetic field and thereby to sense at least one of a position and an orientation of said at least one electrode; and
    wherein said electrode carrier has two carrier parts arranged next to each other configured as two elongated thin rods, wherein the at least one electrode extends between the two rods at the distal end thereof, and said at least one position sensor is arranged at one of said two carrier parts, while an HF supply line for said electrode is arranged in the other one of said two carrier parts.

2. The instrument of claim 1, wherein said at least one position sensor is embedded in a body of said electrode carrier near said at least one electrode.

3. The instrument of claim 1, wherein said at least one position sensor is a coil.

4. The instrument of claim 3, wherein said coil has a coil axis, and said coil is arranged with said coil axis substantially parallel to said longitudinal axis of said electrode carrier.

5. The instrument of claim 1, wherein said elongate electrode carrier has a longitudinal center axis, and said at least one position sensor is arranged outside said longitudinal center axis.

6. The instrument of claim 1, wherein an electrical line connected to said at least one position sensor runs through said one carrier part on which said at least one position sensor is arranged up to a proximal end of said carrier part.

7. The instrument of claim 6, wherein said proximal end of said carrier part on which carrier part said at least one position sensor is arranged is formed as a plug-in contact so that it can be connected to a socket on an instrument housing part of said instrument by axial insertion.

8. The instrument of claim 1, wherein at least a second electromagnetically acting position sensor is provided on said electrode carrier.

9. The instrument of claim 8, wherein said at least one second position sensor is a coil having a coil axis, said coil being arranged substantially with said coil axis transversely in relation to said longitudinal axis of said electrode carrier.

10. The medical instrument of claim 1, wherein said at least one electro-magnetically acting position sensor is arranged to sense the position and the orientation of said at least one electrode when exposed to said magnetic field.

11. A medical system, comprising a medical instrument for the treatment of tissue by means of high-frequency current, said medical instrument comprising:
    an elongate electrode carrier having a longitudinal axis, a distal region, a distal end and a proximal end;
    at least one electrode arranged at said distal end of said electrode carrier which electrode can be supplied with high-frequency current;
    at least one electro-magnetically acting position sensor arranged in said distal region of said electrode carrier immediately adjacent to said at least one electrode, said position sensor being arranged to produce an electrical signal when exposed to a magnetic field and thereby to sense at least one of a position and an orientation of said at least one electrode;
    wherein said electrode carrier has two carrier parts arranged next to each other configured as two elongated thin rods, wherein the at least one electrode extends between the two rods at the distal end thereof, and said at least one position sensor is arranged at one of said two carrier parts, while an HF supply line for said electrode is arranged in the other one of said two carrier parts; and an extracorporeal magnetic-field generator generating said magnetic field for exciting said at least one position sensor.

12. The system of claim 11, further comprising an evaluating device, which evaluates position signals generated by said at least one position sensor with regard to at least one of a position and orientation of said at least one electrode in correlation with a spatial reference.

13. The system of claim 12, further comprising an image generating system, wherein positional information evaluated by said evaluating device is transmitted to said image generating system for the purpose of graphic representation of at least one of a position and orientation of said at least one electrode in relation to said spatial reference.

14. The system of claim 1, further comprising an HF-generator for generating said high-frequency current, and a driving device for driving said magnetic-field generator, which driving device deactivates a high-frequency current supply when said magnetic-field generator is activated, and vice versa.

15. The system of claim 14, further comprising an interlocking circuit which alternately makes possible said high-frequency current supply to said at least one electrode and position sensing by means of said at least one position sensor.

16. The system of claim 11, wherein said magnetic field generated by said magnetic-field generator is an in homogeneous magnetic field.

17. The system of claim 16, wherein said magnetic-field generator comprises tetrahedrally arranged coils generating said inhomogeneous magnetic field.

* * * * *